United States Patent [19]

McRae

[11] Patent Number: Plant 6,328

[45] Date of Patent: Oct. 11, 1988

[54] LILY PLANT NAMED 'RHUMBA'

[75] Inventor: Edward A. McRae, Boring, Oreg.

[73] Assignee: Melridge, Inc., Aurora, Oreg.

[21] Appl. No.: 926,715

[22] Filed: Nov. 4, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of Asiatic hybrid lily plant bearing large clusters of flowers of excellent form and particularly characterized by their deep red-orange coloration, even in the bud stage, the glossy sheen of their upper tepals, their slightly fluted margin and their lack of any spotting. This combination is believed to be completely new in the upright Asiatic divisions of lilies suited to forcing and to mass commercial cultivation. The plant is highly resistant to disease and shows high tolerance of virus, making it an excellent garden plant. The bulbs may be precooled and forced for cut flower production and the clone is vigorous and is a good grower and propagator.

1 Drawing Sheet

BACKGROUND OF THE INVENTION

This new variety of lily plant originated as a seedling selected from a group of seedlings planted by me at Sandy, Oreg., with seeds derived from my crossing a selected seedling from 'Enchantment'×'Connecticut King' (both unpatented) as the seed parent and as the pollen parent, the clonal cultivar 'Rosefire'; this crossing having been made with the objective of producing lilies in the shades of red, well suited to forcing for cut flower production out of season, heretofore unknown in the lily breeding art. This particular seedling was selected for propagation because of its large flowers borne with upright orientation and having, in general, a deep red-orange coloration with an orange center, a color pattern unique in this type of lily. This selected plant has been asexually reproduced by me and under my direction at Sandy, Oreg., with very pleasing results and successive generations of this new plant produced by bulb scale propagation and by natural propagation from bulblets have demonstrated that the novel and distinctive characteristics of this new variety hold true, under asexual propagation, from generation to generation and appear to be firmly fixed. Extensive propagation of this new plant has demonstrated that the clone possesses to a high degree the desirable characteristics of hybrid vigor, great hardiness, as well as all of the desired characteristics of excellence of form, color and habit, as well as being vigorous and a good grower and propagator as observed at Sandy, Oreg.

DESCRIPTION OF THE DRAWING

My new variety of lily plant is illustrated by the accompanying full color photographic drawing, which shows buds and an open bloom and illustrates the flower form, the tepal arrangement and particularly, the novel and distinctive unspotted tepals having lightly fluted margins.

DESCRIPTION OF THE NEW VARIETY

The following is a detailed description of my new variety of Asiatic hybrid lily with nomenclature according to The International Lily Register of The Royal Horticultural Society of London (Second Edition, 1969), and with color designations according to The R.H.S. Colour Chart (1966).

THE PLANT

Origin: Seedling.

Parentage:

*Seed parent.*—A selected seedling from 'Enchantment'×'Connecticut King' (both unpatented).

*Pollen parent.*—Lilium 'Rosefire' (unpatented).

Classification:

*Horticultural.*—Division I-A, Upright Asiatic Hybrid Lily, according to The Horticultural Classification of Lilies by The Royal Horticultural Society of London.

*Commercial.*—Hybrid Lilium Clone.

Form: Single stem, erect and stately.

Height: About 100 to 120 cm. for stems produced by glasshouse forcing of bulbs having a circumference of about 15 to 18 cm. provided that their light levels are adequate.

Growth: Vigorous and upright.

Foliage:

*Quantity.*—Abundant.

*Leaf size.*—About 8 to 14 cm. long and about 1 to 2 cm. wide.

*Leaf shape.*—Lanceolate with acute apex.

*Texture.*—Leathery.

*Aspect.*—Glossy.

*Color.*—Dark green; somewhat lighter on the lower side.

Bulbs:

*Size.*—Various, depending upon age, and ranging to about 25 cm. in circumference in commercial use.

*Color.*—White.

THE BUD

Form: Long ovoid with rounded base and acute apex.

Size: About 8 to 9 cm. long and about 5 cm. in circumference just prior to opening.

Opening rate: The bud opens slowly, taking about one hour in response to morning light.

Color: Varying from medium to deep orange and to slightly red-orange just prior to opening and as the tepals begin to unfurl.

Peduncle:

*Length.*—Averages about 4 to 6 cm., but may be slightly longer if light levels are too low.

*Color.*—Dark green with light plum overlay.

THE FLOWER

Blooming habit: Once annually and profusely in midseason for Asiatic lilies.

Size: Large, about 14 to 16 cm. in diameter.

Borne: As a single racemose inflorescence having about 8 to 10 buds from a bulb of about 12 to 15 cm. in circumference.

Shape: Cup-shaped when first opening and flattening somewhat as the tepals recurve during the second day.

Tepalage:

*Number.*—Six.

*Arrangement.*—Hexgonal and imbricated.

*Shape.*—Ovate with lightly fluted and entire margins.

*Size.*—Outer tepals — About 2.5 cm. wide, in average. Inner tepals — Averaging about 3 cm. wide.

*Appearance.*—Shiny.

*Color.*—The base color is deep red-orange, RHS 33A to 34B. A rich orange flush, RHS 28A, about 1 cm. wide, extends 2 to 3 cm. from the nectaries, which are glabrous and green overlaid with soft plum. Also, there is a deeper flush of plum, RHS 59D, about 1 cm. wide overlaying the red-orange color at the base of each tepal.

*Tepal Spotting.*—The tepals are entirely unspotted.

*Tepal longevity.*—The tepals stay on the stems about 3 weeks.

*Color changes.*—The flower fades only slightly, becoming slightly more orange and slightly less red-orange as the flower ages, with light levels adequate for cut flower maintenance.

Pedicel:

*Length.*—Averaging from 4 to 10 cm.

*Form.*—Sturdy and ascending up to 45° from the horizontal and very rarely having secondary buds.

*Color.*—Dark green.

Fragrance: None.

Disease resistance: The flower and plant are resistant to disease, particularly they are resistant to Botrytis blight and to Fusarium bulb rot.

Lasting quality: The flower is long lasting, both on the plant and as a cut flower.

THE REPRODUCTIVE ORGANS

Stamens:

*Number.*—Six.

*Arrangement.*—Typical of the genus Lilium.

*Filaments.*—Length: About 5 cm. Color: Soft red, RHS 47C.

*Pollen and dehisced anthers.*—Color: Greyed orange, RHS 171A.

Pistils:

*Number.*—One.

*Style.*—About 5 cm. long.

*Stigma.*—Size: Small. Color: Soft red with deep plum overlay.

Character of ovary: Typical of genus Lilium.

THE FRUIT

Fertility: The fruit is fertile.

Shape: Ovoid.

Color at maturity: Soft brown, sometimes overlaid with soft plum.

This new variety of lily plant most closely resembles 'Rosefire' but it is distinguished by having flowers which are more of a bicolor blend of a deeper orange throat suffusing into a deep red-orange margin; whereas 'Rosefire' has a golden yellow center and a deep orange margin. Also, the new plant has slightly fluted petals, unlike those of 'Rosefire'.

I claim:

1. A new and distinct variety of Asiatic hybrid lily, substantially as herein shown and described, characterized by its large, glossy, and unspotted flowers of deep red-orange coloring with wide tepals having slightly fluted margins; its vigorous growth and rapid natural propagation; and its versatility both as a garden plant and as a cut flower producer from precooled bulbs forced out of season under glass.

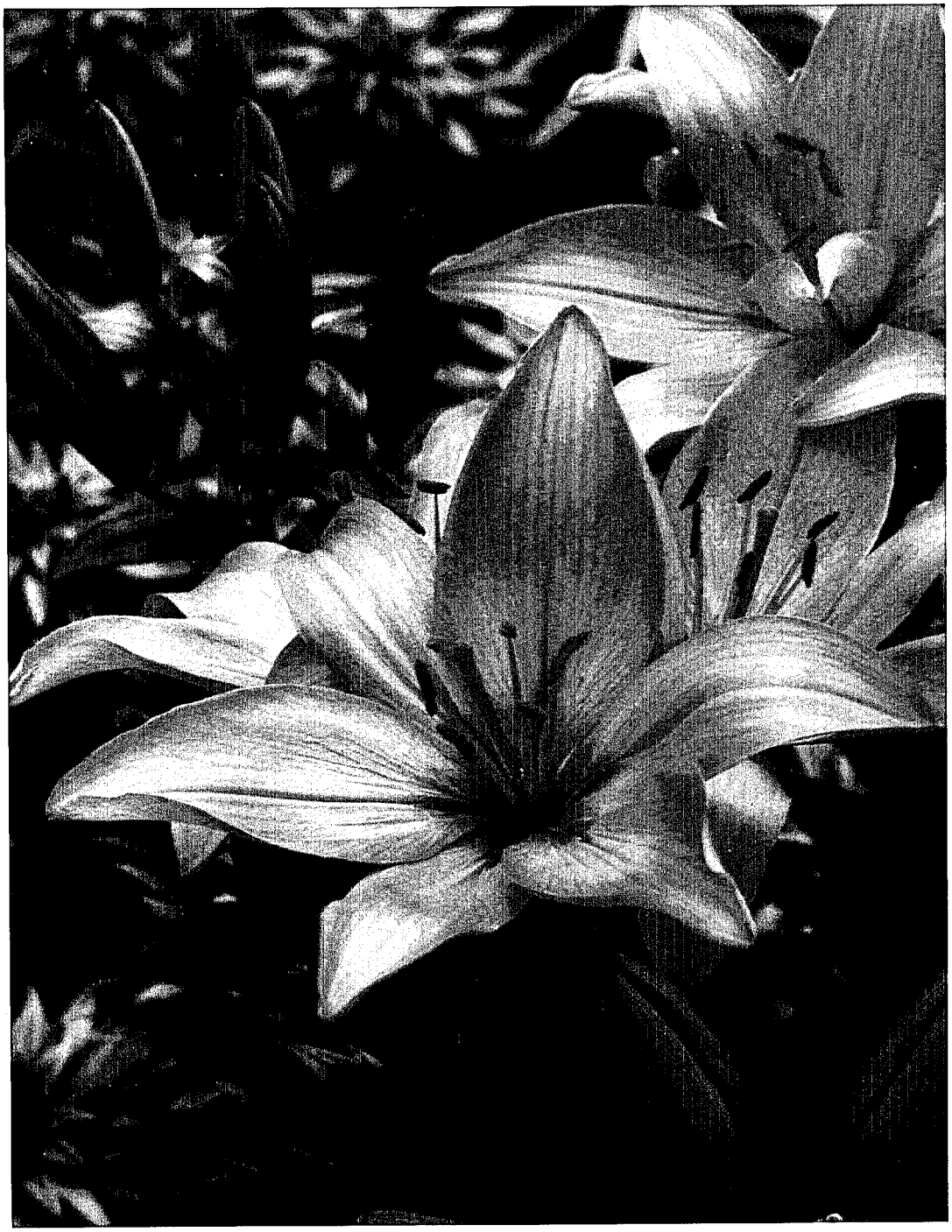

* * * * *